(12) United States Patent
Montalban

(10) Patent No.: US 9,642,679 B2
(45) Date of Patent: May 9, 2017

(54) RAPID PALATAL EXPANDER

(71) Applicant: VISOTTICA INDUSTRIE S.p.A, Susegana (IT)

(72) Inventor: Rinaldo Montalban, Venice (IT)

(73) Assignee: VISOTTICA INDUSTRIE S.P.A., Susegana (TV) (IT)

( * ) Notice: Subject to any disclaimer, the term of this patent is extended or adjusted under 35 U.S.C. 154(b) by 256 days.

(21) Appl. No.: 14/332,400

(22) Filed: Jul. 16, 2014

(65) Prior Publication Data
US 2015/0024334 A1 Jan. 22, 2015

(30) Foreign Application Priority Data
Jul. 17, 2013 (IT) ............................... PD2013A0196

(51) Int. Cl.
A61C 7/10 (2006.01)
(52) U.S. Cl.
CPC ..................................... A61C 7/10 (2013.01)
(58) Field of Classification Search
CPC ....................................................... A61C 7/10
USPC ................................................ 433/7, 10, 12
See application file for complete search history.

(56) References Cited

U.S. PATENT DOCUMENTS

| 3,284,902 | A | * | 11/1966 | Dillberg | ................... | A61C 7/10 |
| | | | | | | 433/7 |
| 5,281,133 | A | | 1/1994 | Farzin-Nia | | |
| 5,439,377 | A | | 8/1995 | Milanovich | | |
| 6,783,361 | B2 | | 8/2004 | Huge et al. | | |
| 7,837,465 | B2 | | 11/2010 | Forster | | |
| 2004/0152033 | A1 | | 8/2004 | Collins | | |
| 2007/0275341 | A1 | | 11/2007 | Hanks | | |
| 2010/0112507 | A1 | * | 5/2010 | Ehrenberger | ............ | A61C 7/10 |
| | | | | | | 433/7 |

FOREIGN PATENT DOCUMENTS

| DE | 10 2007 002040 | 7/2008 |
| EP | 1247498 | 10/2002 |
| FR | 2193322 | 2/1974 |
| WO | 03/071976 | 9/2003 |
| WO | 2012/120447 | 3/2012 |
| WO | 2012/042547 | 4/2012 |

* cited by examiner

Primary Examiner — Cris L Rodriguez
Assistant Examiner — Hao D Mai
(74) Attorney, Agent, or Firm — Mark M. Friedman

(57) ABSTRACT

Rapid palatal expander which has an actuator element provided with a drive head and with two threaded stems, as well as a first and a second main bodies provided with aligned female threads, each engaged by a threaded stem of the actuator element for guiding a simultaneous movement of the main bodies. A plurality of longitudinal seats are provided on a peripheral surface of the drive head. A plate is connected to one of the two main bodies and is provided with a flexible tab elastically in abutment against the peripheral surface of the drive head and able to be selectively engaged with its profile in the longitudinal seats of the head at angular adjustment positions assumed by the latter.

19 Claims, 15 Drawing Sheets

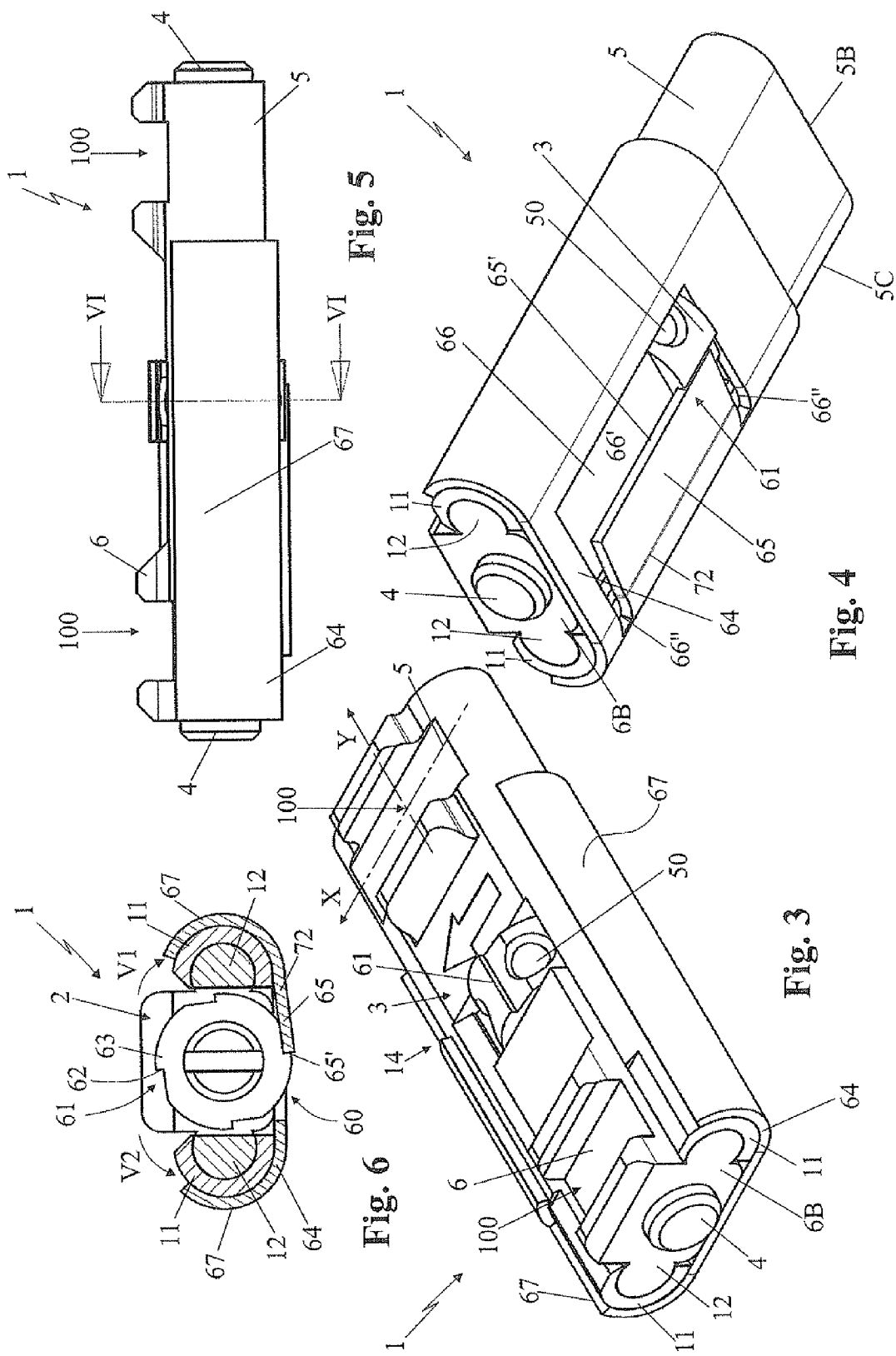

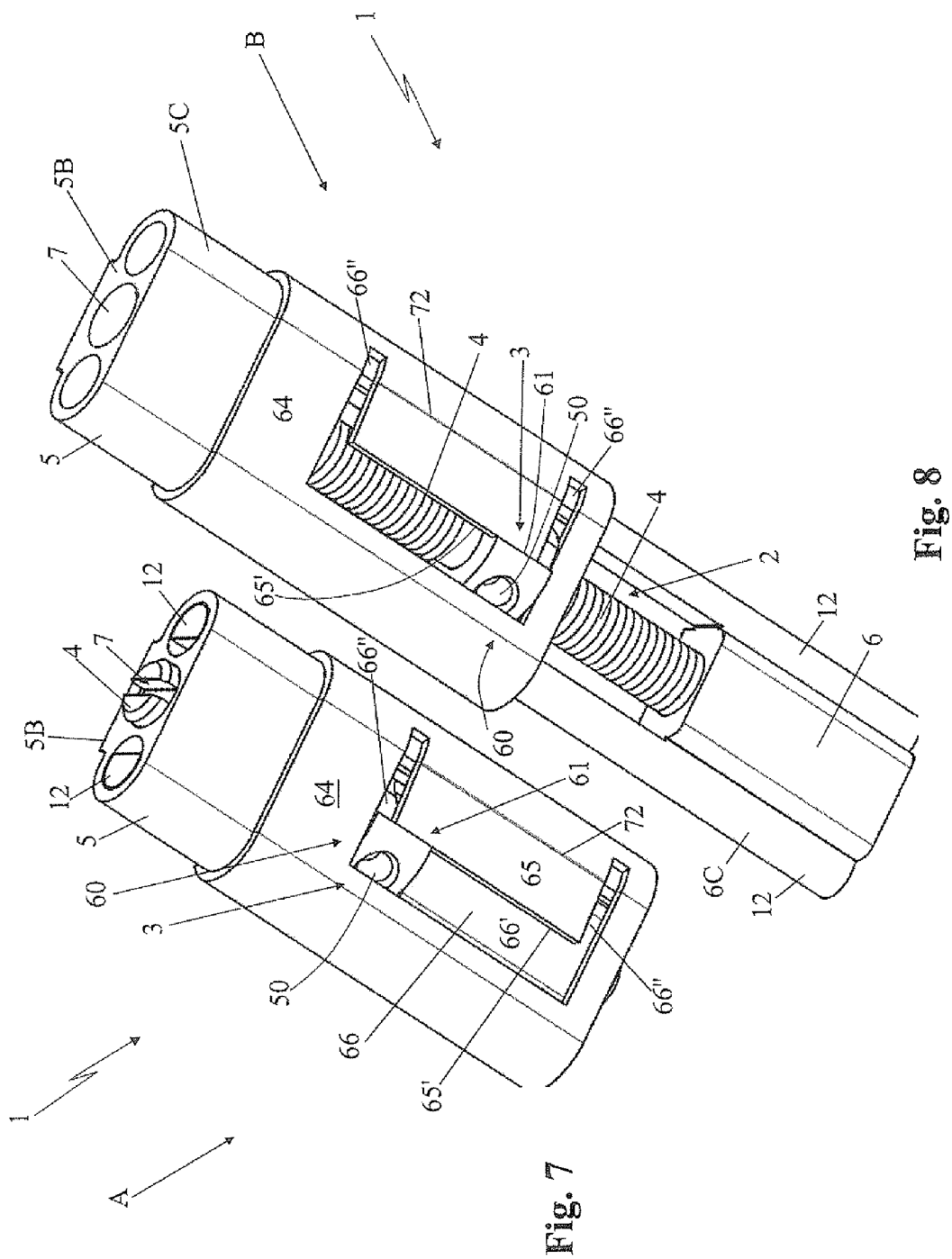

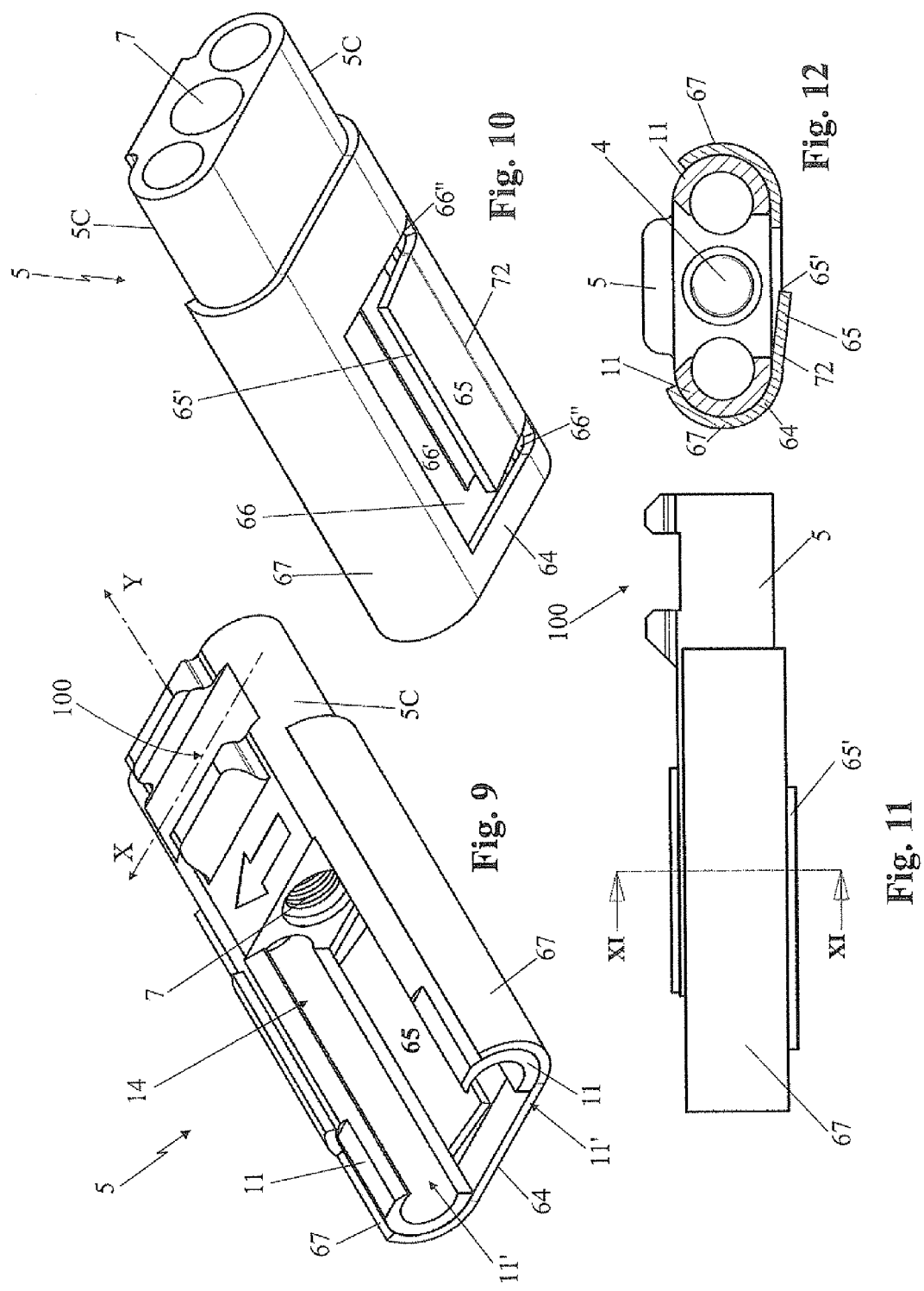

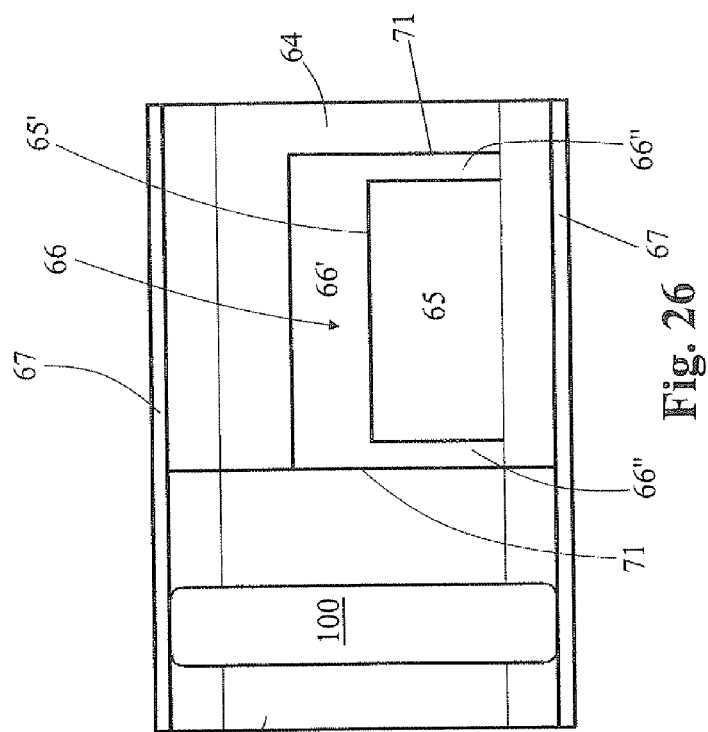
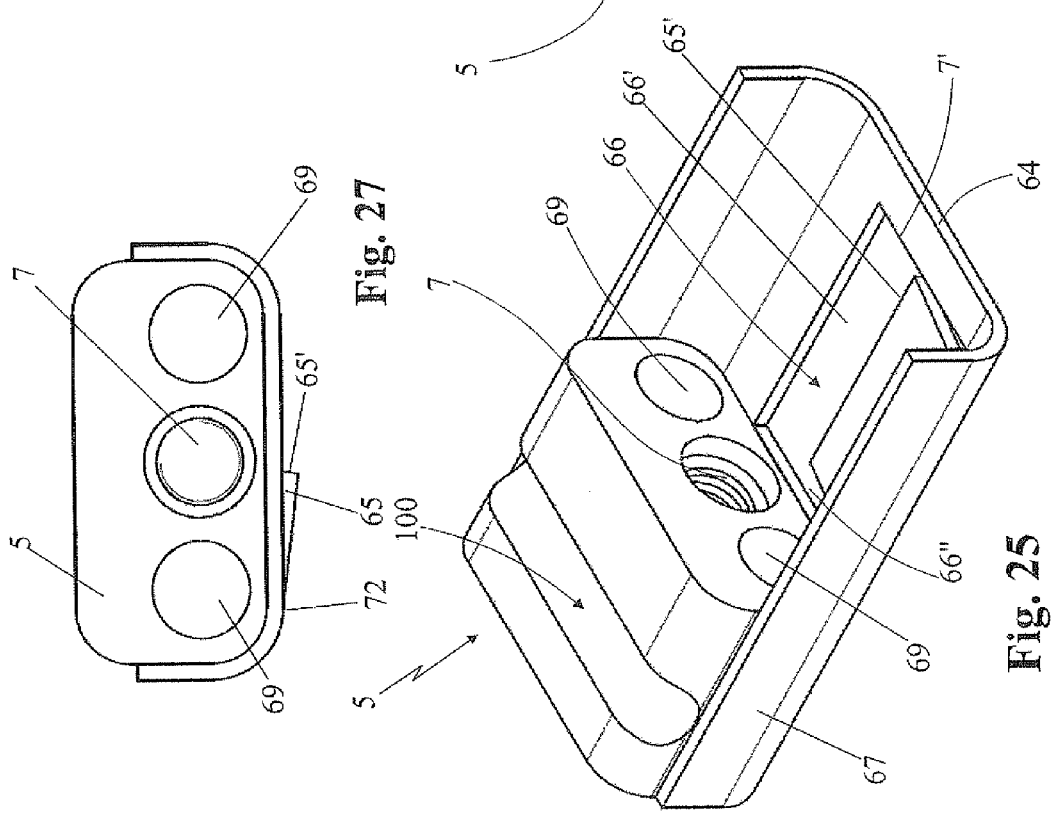

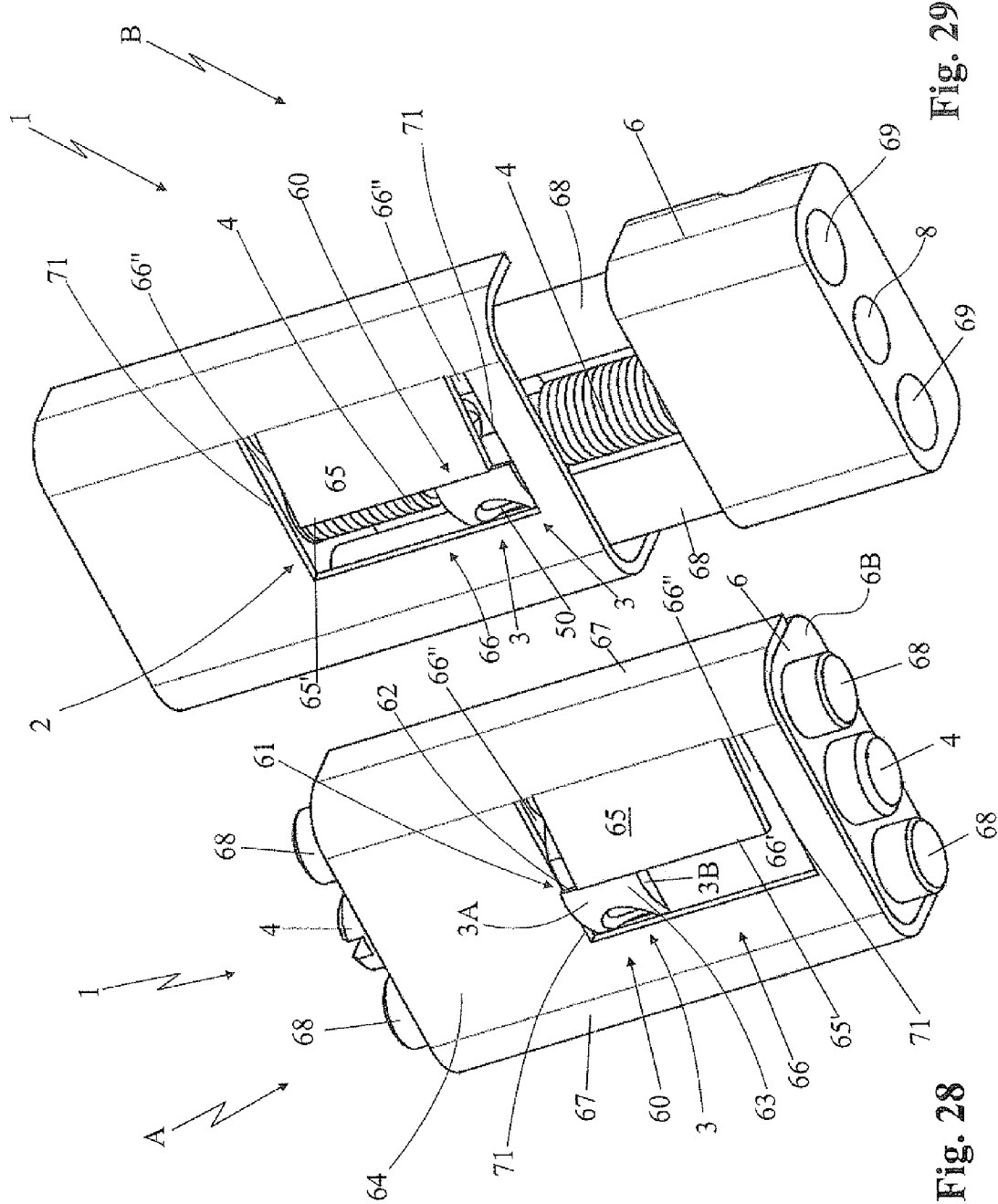

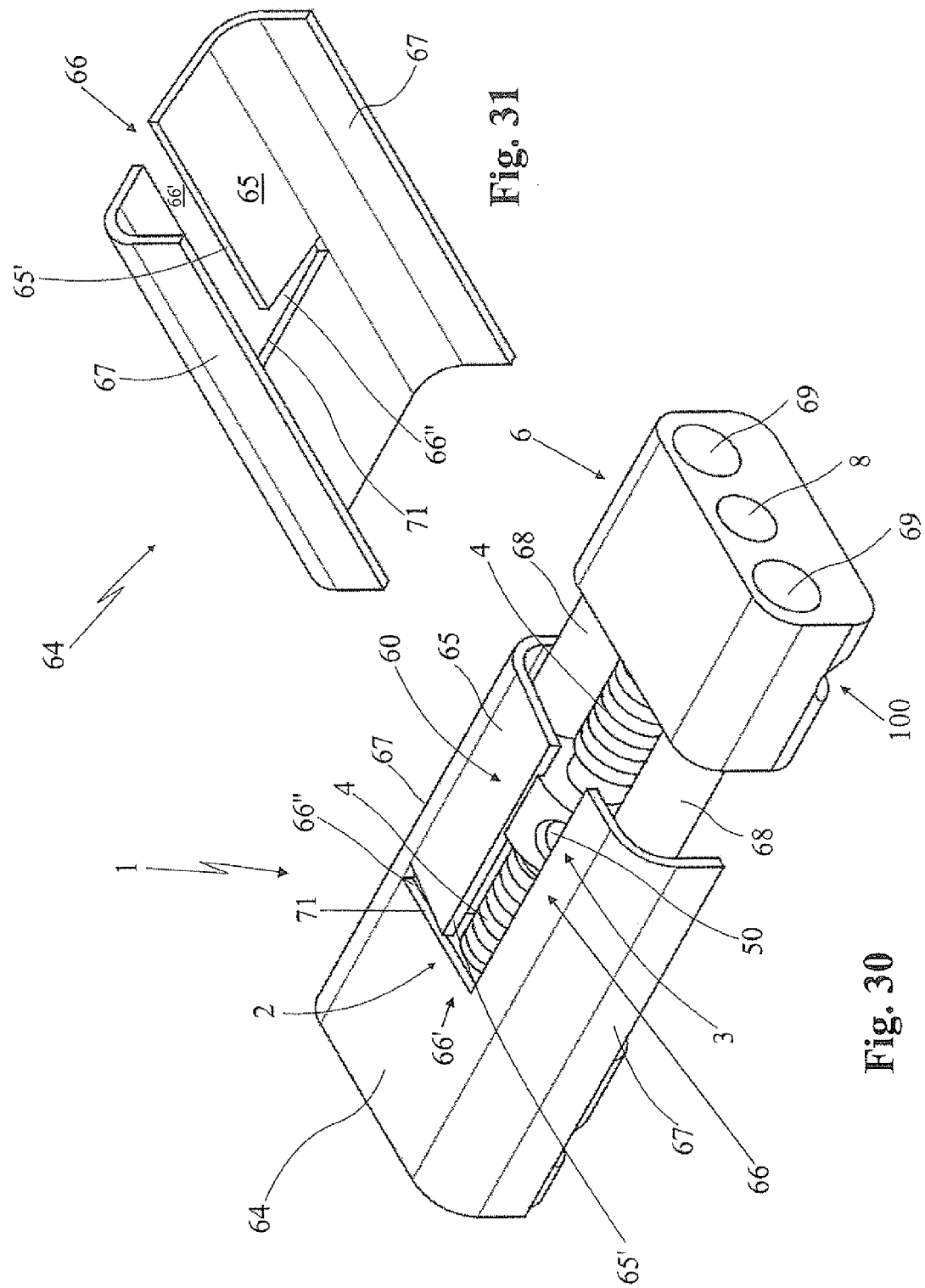

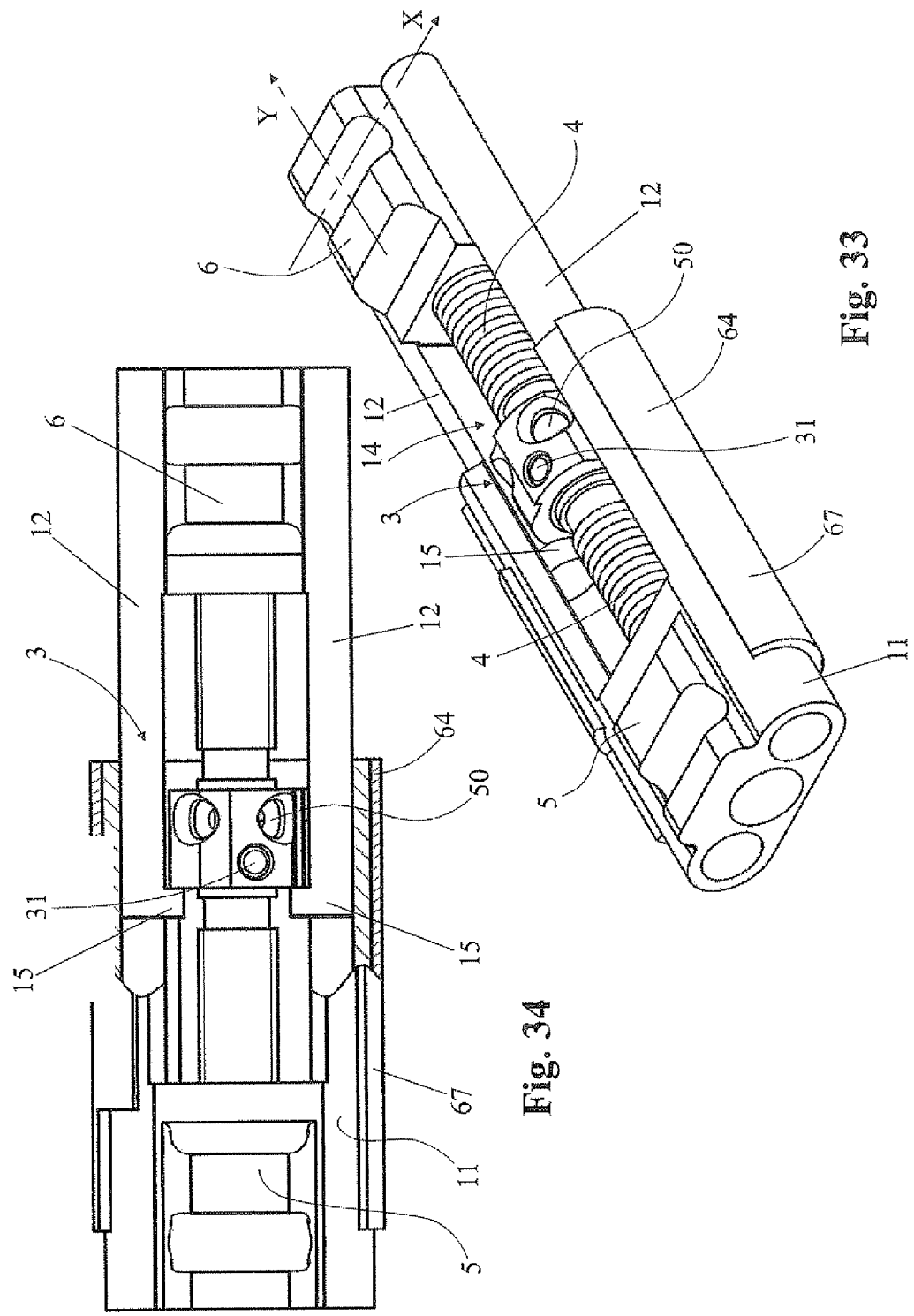

RAPID PALATAL EXPANDER

FIELD OF APPLICATION

The present invention regards a rapid palatal expander, according to the preamble of the independent claim.

The present rapid palatal expander, otherwise termed expander or spreader in the technical jargon of the field, is advantageously intended to be employed in the orthodontics field for the treatment of cases of skeletal hypoplasia of the upper jaw, especially for subjects during development, before the end of puberty, when the median suture of the palate is not yet completely ossified.

It is an instrument that is applied in the mouth for a period of time and which causes the mechanical widening of the palate in a manner so as to create more space between the two rows of the upper dental arch.

The rapid palatal expander is therefore an orthodontics instrument and more generally a dental-maxillo-facial aid employable for the correction of a pathological condition of transverse growth deficit of the upper jaw, which can involve a poor dental occlusion, and can also have repercussions on phonesis, deglutition as well as respiration.

Therefore, the rapid palatal expander, object of the present invention, is inserted in the field of the orthodontic devices and the maxillo-facial devices.

STATE OF THE ART

Different mechanical solutions of rapid palatal expanders (with ERP initials) are known in the orthodontics field and have been for some time employed for the correction of the transverse growth deficit of the upper jaw. Such known expanders are based on the same mechanical principle of moving two bodies away from each other with the use of a screw engaged thereto, of twin and opposite thread type. More in detail, the palatal expanders of conventional type present on the market commonly have a support structure comprising:

- two main bodies mechanically connected to two or more rigid arms which are extended in opposite directions, and are intended to interact, by means of anchorage bands (e.g. molar bands) or other mechanical elements, with corresponding opposite portions of the dental arch;
- an elongated twin-screw actuator element provided with a drive head with cylindrical form arranged in a median position thereof, and with two stems with threads with opposite senses obtained, such stems extended aligned in opposite directions, starting from the drive head, until they are engaged in threaded seats of the two main bodies; the drive head is peripherally provided with holes for the insertion of a key adapted to allow the rotation of the twin-screw element for the mutual moving apart or approaching of the two main bodies and hence of the molar bands that act on the arch;
- one or two guide pins, which are slidably inserted inside corresponding holes obtained in the two main bodies, in order to guide the translation of the latter following the driving in rotation of the twin-screw element.

Several embodiments of rapid palatal expanders of the above-described known type are described in the patents WO-A-2012120447, EP-A-1247498. These are produced by assembling together numerous components, each of which obtained with their own normal production tolerances. In particular, each guide pin slides with clearance in at least one hole of a main body, which is translated into a functioning that is not very fluid, with inefficient mechanical transmission at the terminations of the arms.

In addition, obtaining the expanders with a considerable number of components implies production times and costs that are clearly quite high.

A very important need in the field of rapid palatal expanders lies in preventing the two main bodies from reapproaching each other during the normal use of the expander, which would consequently involve reduced expansion action transmitted by the bodies to the teeth by means of the rigid aims and the anchorage bands.

Such reapproaching is due to the fact that the actuator element can rotate backward with respect to the position already reached by means of the previous actuation of the key. Such undesired rotation depends on the fact that the various stresses to which the expander is subjected inside the oral cavity, such as normal chewing, can make the head of the twin-screw actuator element rotate in the sense opposite that which determines the expansion, thus actually canceling the action itself of the expander.

In order to prevent this drawback, rapid palatal expanders have been designed with so-called "anti-return" mechanisms which can prevent such drawback.

Known from the patent WO-A-2012042547 is a rapid palatal expander, in which the head of the actuator element is housed in a seat defined by two opposite grooves obtained on the two parallel guide pins. The head has a ribbing radially projecting from its circumferential surface, which is susceptible to exert a pressure on the guide pins so as to determine a friction rotation due to friction of the screw actuator, which limits the involuntary rotations in the opposite sense which, as said, would bring the palatal spreader to be closed, by approaching the two main bodies.

A first drawback lies in the fact that the friction force in reality limits but does not entirely prevent the undesired rotation of the screw actuator.

A further drawback lies in the fact that for the assembly of the expander, it is necessary to force the two guide pins into the respective seats up to the insertion of the head in the two grooves of the guide pins.

Known from the U.S. Pat. No. 5,281,133 is a rapid palatal expander, in which the head of the actuator element has a plurality of niches distributed at regular distance on the external surface thereof. A plate is mounted on the guide pins and is provided with a projecting nose section which is susceptible to being snap-inserted in the niches of the head when the latter is made to rotate by the key, so as to define stable adjustment positions capable of preventing the opposite rotation of the head during expander use.

One drawback of this expander embodiment lies in the fact that in practice, the projecting nose section is not able to define a safe check for the head of the actuator element, due to the limited size of the various members that make up the expander and the tolerances at play.

An expander similar to that described above is indicated in the U.S. Pat. No. 7,837,465, in which in place of the plate, a friction brake is provided that is obtained with a metal elastic strap fixed as a bridge to a pair of parallel guide pins that are free to slide in holes obtained in the two main bodies. The strap is maintained under pressure on the head of the actuator element in order to exert a constant pressure thereon aimed to oppose any one involuntary rotation thereof and hence also a rotation aimed to reapproach the two main bodies.

Also for this expander, as already described in the patent WO 2012-A-042547, the friction force only limits the possibilities of the actuator element to rotate towards closure.

In addition, the absence of reference marks, such as notches or the like, does not allow having a precise adjustment in the rotation of the head of the actuator element and hence of the force exerted by the expander.

The U.S. Pat. No. 7,384,265 describes a rapid palatal expander, in which the head of the actuator element has a plurality of niches distributed at regular distance on the external surface, as already described for the expander of the U.S. Pat. No. 5,281,133. In this case, however, instead of a plate a spring piston is provided, mounted fixed on a guide pin in median position; such piston is provided with a fixed support body provided with a seat in which an engagement element provided with rounded tip is slidably inserted. Such element is elastically pushed by a spring to slide against the head of the actuator element, in order to selectively insert its rounded tip in the various niches of the actuator element head when the latter is made to rotate for the adjustment of the expander pressure.

Such embodiment has the advantage of absorbing, with the spring, the possible clearances due to the tolerances in mounting the different components; nevertheless, it has the serious drawback of being extremely complex and costly to obtain.

The U.S. Pat. No. 6,783,361 describes an expander with anti-return mechanism for the rotation of the actuator element similar to the preceding expander; here, in place of the spring piston, a "ratchet" mechanism is fixed to the guide pin. The latter comprises an elastically flexible metal strap that projects above the lateral surface of the head of the actuator element. Such head is provided with a plurality of longitudinal grooves that define steps with coupling faces directed in the non-return sense, which are selectively engaged by the front edge of the metal strap in order to prevent the screw actuator element from rotating backward, closing the expander.

As with the preceding embodiment, also the latter has the disadvantage of being extremely complex and costly to obtain.

Analogously, also the patent FR-A-2193322 describes an expander with anti-return mechanism for the rotation of the actuator element in which at one of the guide pins, an elastically flexible metal strap is fixed which projects above a ratchet mechanism fixed laterally to the head of the actuator element. Such ratchet mechanism is provided with a plurality of grooves that define steps with coupling faces directed in the non-return sense, which are selectively engaged by the front edge of the metal strap in order to prevent the screw actuator element from rotating backward, closing the expander.

As with the previous embodiment, also the latter has the disadvantage of being extremely complex and costly to obtain.

A further limit of various rapid palatal expanders of known type lies in the fact that they do not have an end stop that stops the moving apart of the two main bodies and prevents an involuntary excessive separation of the same two main bodies from having them disengage from the thread of the twin-screw element, determining the disassembling of the palatal expander in the mouth of the patient during its activation.

The end stop of the palatal expanders is, as known, constrained by the shape and size of the guide pins, of the anti-rotation mechanisms and of the main bodies which must be stopped in their expansion travel.

Palatal spreaders of the above-described conventional type, provided with end stops in the opening are in any case known, for example from the U.S. Pat. No. 4,482,318. The latter describes a palatal expander, in which the two guide pins have enlarged ends with radially projecting edges, susceptible to abut against a shoulder obtained at the holes of the opposite main bodies when the same main bodies are moved away from each other in the position of their maximum expansion. Such solution has proven rather difficult to achieve, in particular since rather than providing for simple holes in the main bodies, shaped holes are provided i.e. equipped with shoulders in order to act as stops of the guide pins.

Presentation of the Invention

In this situation, the problem underlying the present invention is to eliminate the drawbacks of the abovementioned prior art, by providing a rapid palatal expander, which during its use by the patient does not involuntarily reduce the expansion reached with its progressive adjustments.

A further object of the present finding is to provide a rapid palatal expander, which is structurally simple and entirely reliable in operation.

A further object of the present finding is to provide a rapid palatal expander, which is inexpensive to obtain.

A further object of the present finding is to provide a rapid palatal expander, which is entirely safe for the patient who wears it.

These and still other objects are all achieved by the rapid palatal expander, object of the present invention, which comprises a rod-shaped actuator element with main extension in a longitudinal direction, provided with a drive head in a median position thereof and having a substantially cylindrical peripheral surface coaxial with the longitudinal direction, and with two stems, which are extended aligned in opposite directions from the drive head with threads in opposite senses; a first and a second main body provided with corresponding opposite first and second front face with respective aligned female threads obtained, each engaged by a threaded stem of the actuator element; guide means for guiding the simultaneous movement of the main bodies along the longitudinal direction following the rotation of the drive head in at least one first rotation sense for at least one adjustment travel of the main bodies, from at least one collected position, in which the main bodies are close to each other, to at least one expanded position, in which the main bodies are spaced from each other; anti-rotation means for preventing the rotation of the drive head of the actuator element in the second rotation sense opposite the first rotation sense, which comprise a plurality of equidistant longitudinal seats obtained on the peripheral surface of the drive head, each having an abutment face at least partially directed in the second rotation sense.

According to the idea underlying the present invention, the rapid palatal expander is characterized in that the anti-rotation means further comprise a plate mechanically and rigidly connected to a first of the two main bodies, provided with a flexible tab being extended in the longitudinal direction, arranged elastically in abutment against the peripheral surface of the drive head, for the adjustment travel of the first main body; the flexible tab being adapted to be selectively engaged with an engagement profile thereof in the longitudinal seats at angular adjustment positions assumed by the drive head along the adjustment travel.

BRIEF DESCRIPTION OF THE DRAWINGS

The technical characteristics of the finding, according to the aforesaid objects, can be clearly seen in the contents of the below-reported claims, and the advantages thereof will be more evident from the following detailed description made with reference to the enclosed drawings, which represent several merely exemplifying and non-limiting embodiments of the invention, in which:

FIG. 3 shows a top perspective view of the rapid palatal expander of FIG. 2, assembled and in closed position;

FIG. 4 shows a bottom perspective view of the rapid palatal expander of FIG. 2, assembled and in closed position;

FIG. 5 shows a side view of the rapid palatal expander of FIG. 2, assembled and in closed position;

FIG. 6 shows a front view in section of the assembled expander of FIG. 2, carried out along the line VI-VI of FIG. 5;

FIGS. 7 and 8 show the expander of FIG. 2, assembled and respectively in a closed position (or minimum expansion position) and in an open position (or maximum expansion position);

FIG. 9 shows a top perspective view of a detail of the rapid palatal expander of FIG. 3 relative to a female main body;

FIG. 10 shows a bottom perspective view of the detail of the rapid palatal expander of FIG. 9;

FIG. 11 shows a side view of the detail of the rapid palatal expander of FIG. 9;

FIG. 12 shows a front view in section of the detail of the expander of FIG. 9, carried out along the line XI-XI of FIG. 11;

FIG. 25 shows a perspective view of a detail of the rapid palatal expander of FIG. 22 relative to one of the two main bodies with an anti-rotation plate fixed;

FIG. 26 shows a top view of the detail of FIG. 25;

FIG. 27 shows a front view of the detail of FIG. 25;

FIGS. 28 and 29 show the expander of FIG. 22, assembled and respectively in a closed position (or minimum expansion position) and in an open position (or maximum expansion position);

FIG. 30 shows a bottom perspective view of a third embodiment of a rapid palatal expander with several parts removed (the arms for transmitting the pressure to the teeth anchoring bands) in order to better illustrate other parts;

FIG. 31 shows a perspective view of a detail of the rapid palatal expander of FIG. 30 relative to an anti-rotation plate;

FIG. 33 shows a top perspective view of the embodiment of a rapid palatal expander of FIG. 32 in an open position (or maximum expansion position);

FIG. 34 shows a plan view of the expander of FIG. 33, in open position, and with several details relative to a pair of female rods in section according to a plane parallel to the lying plane of the same rods, in order to better underline the presence of their nose sections.

DETAILED DESCRIPTION OF A PREFERRED EMBODIMENT

Figure 1:
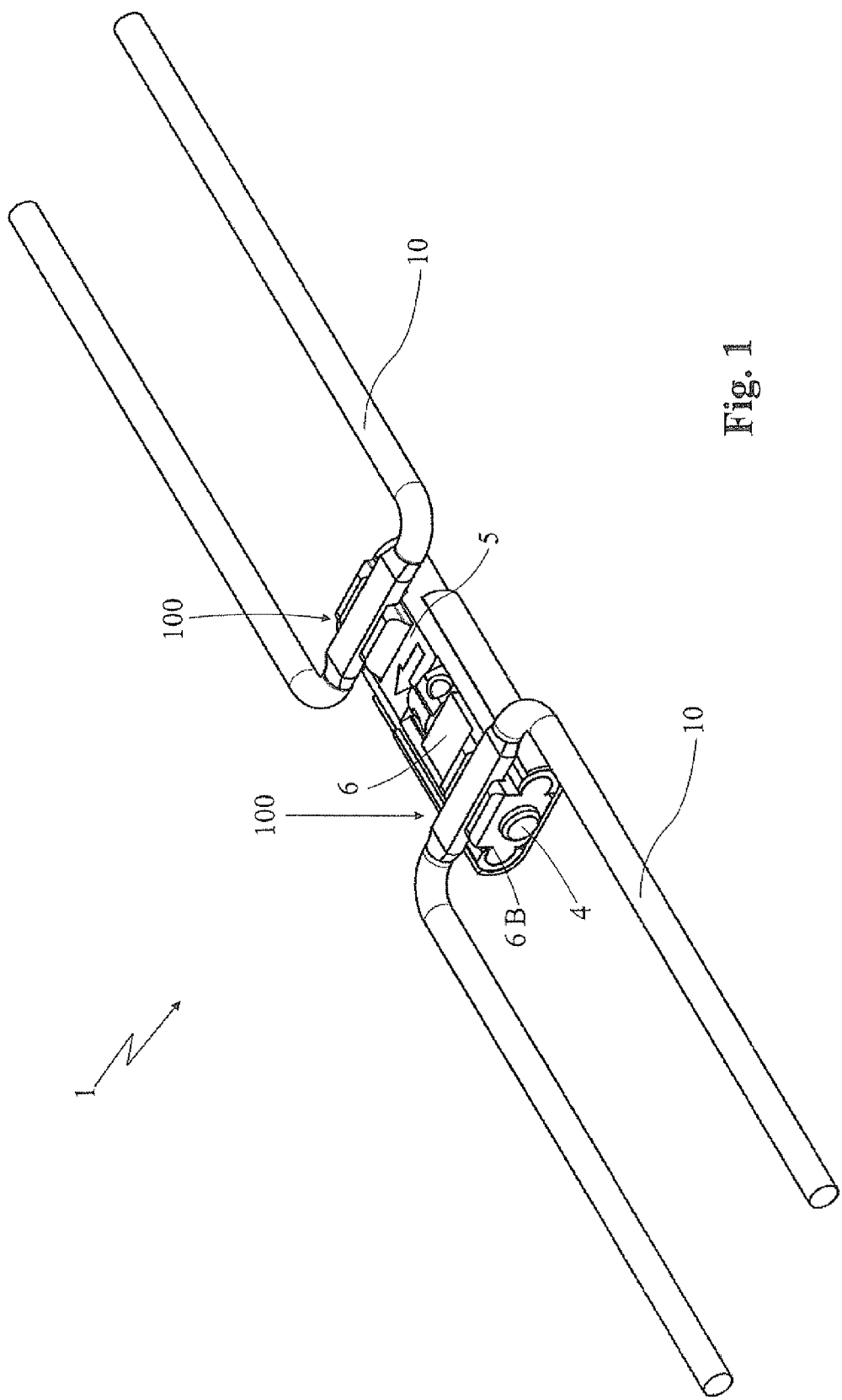
FIG. 1 shows a general perspective view of a first embodiment of the rapid palatal expander according to the present invention.
Figure 2:
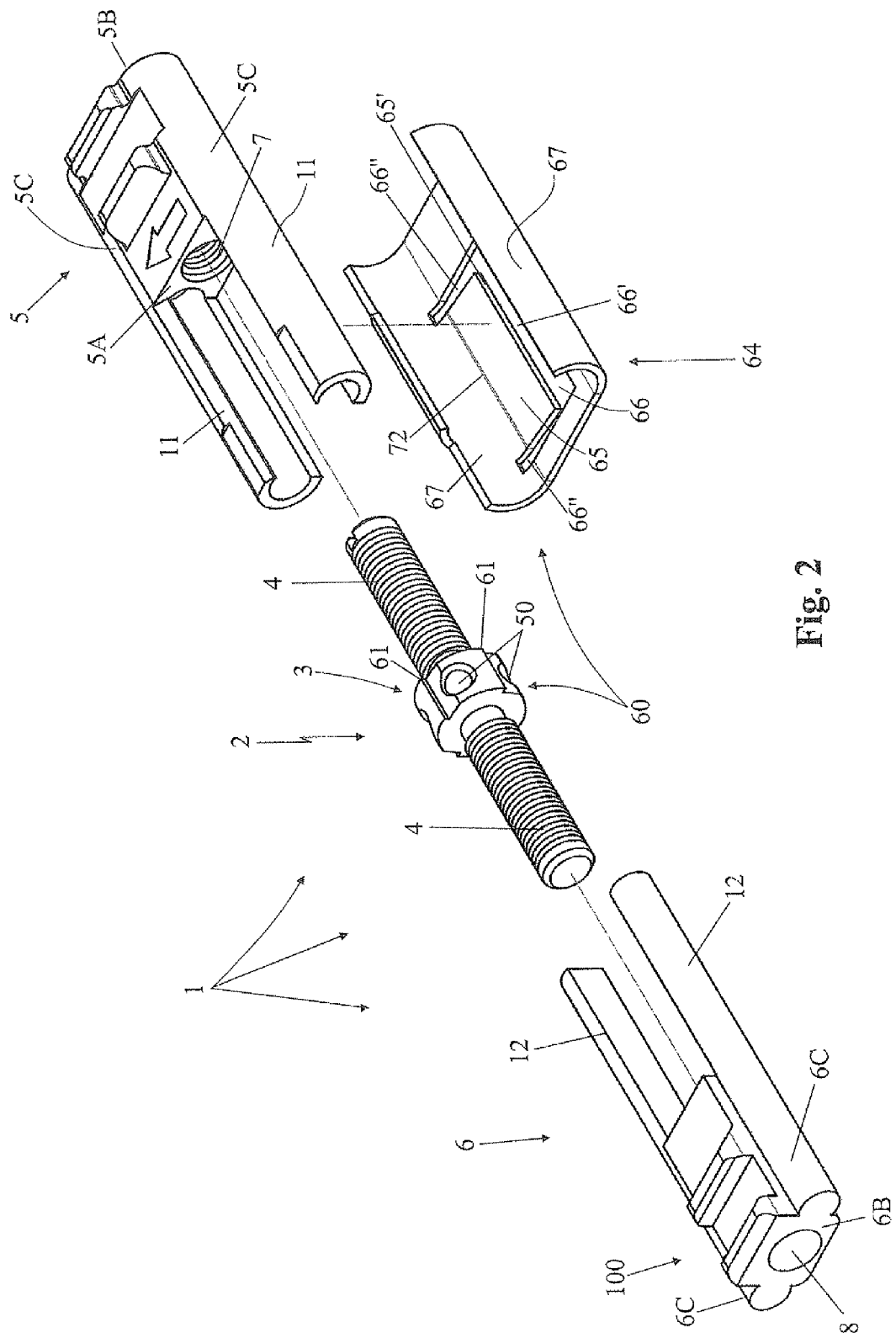
FIG. 2 shows an exploded perspective view of the rapid palatal expander of FIG. 1 with several parts removed (the arms for transmitting the pressure to the teeth anchoring bands) in order to better illustrate other parts.
Figure 14:
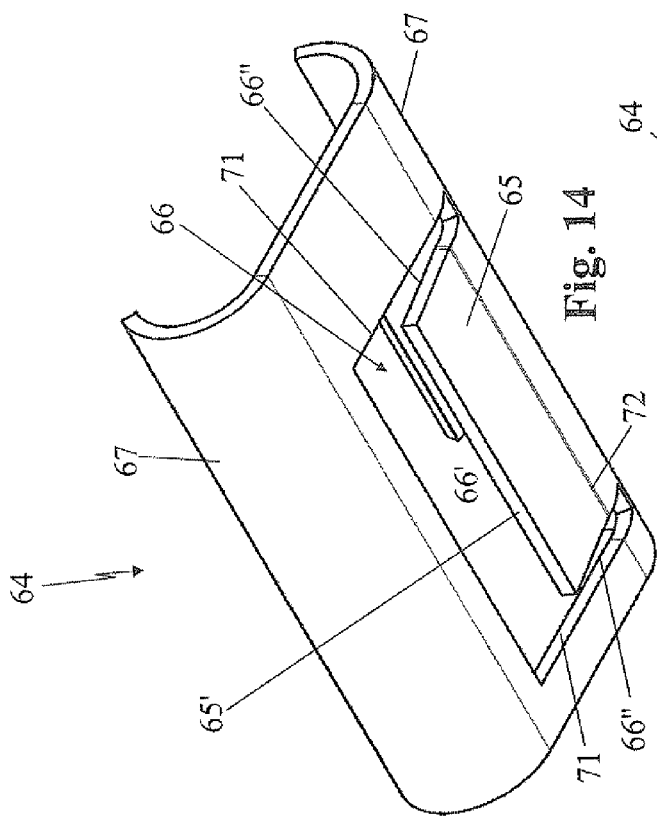
FIG. 14 shows a bottom perspective view of the detail of the rapid palatal expander of FIG. 13.
Figure 15:
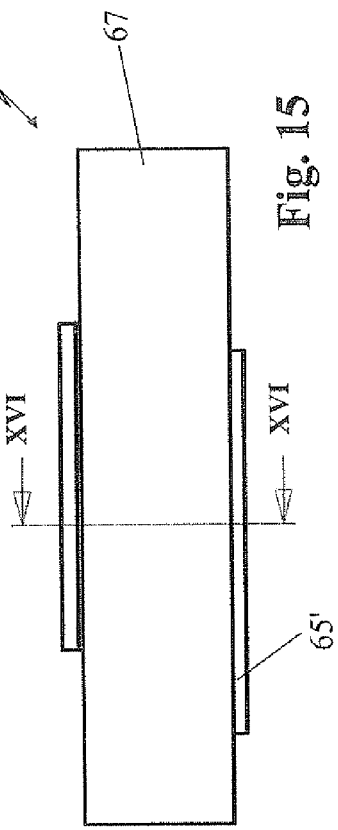
FIG. 15 shows a side view of the detail of the rapid palatal expander of FIG. 13.
Figure 13:
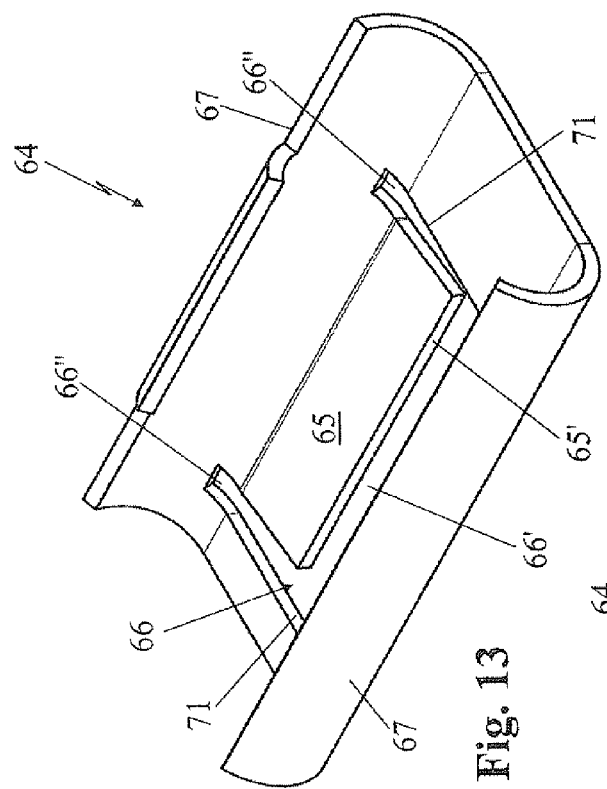
FIG. 13 shows a top perspective view of a detail of the rapid palatal expander of FIG. 3 relative to an anti-rotation plate.
Figure 16:
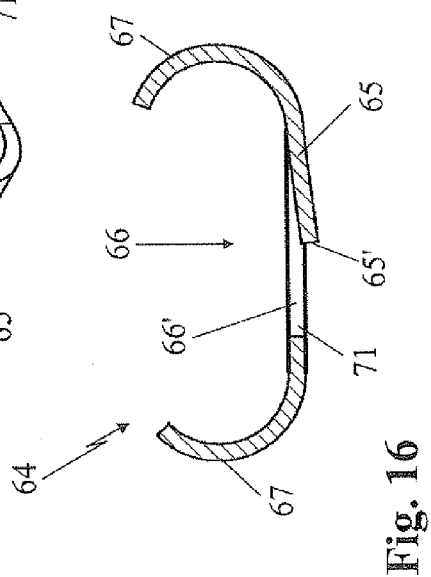
FIG. 16 shows a front view in section of the detail of the expander of FIG. 13, carried out along the line XVI-XVI of FIG. 16.
Figure 18:
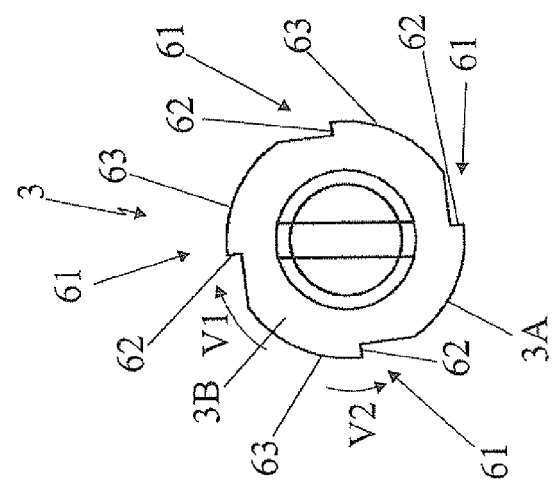
FIG. 18 shows a front view of the detail of the rapid palatal expander of FIG. 17.
Figure 17:
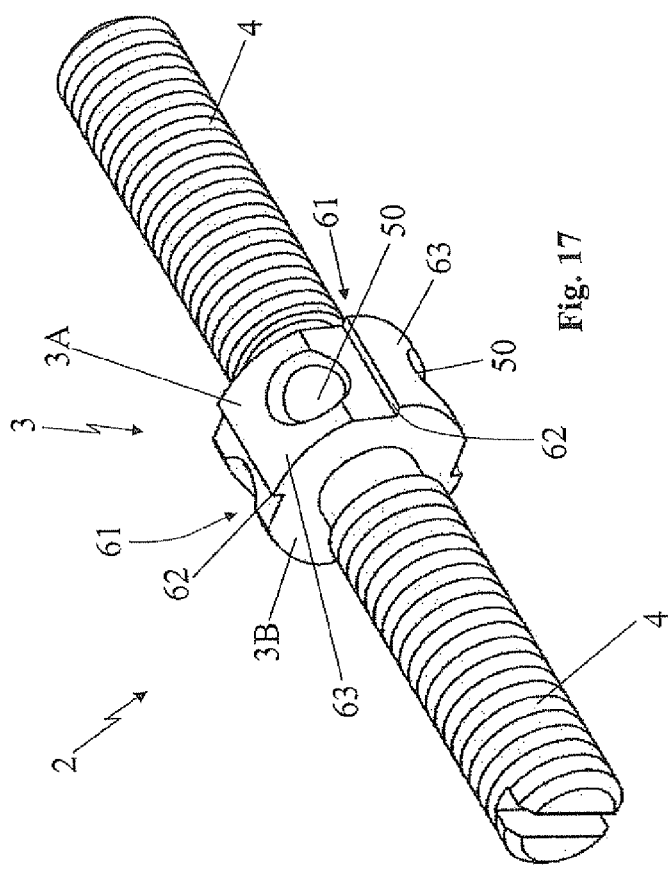
FIG. 17 shows a perspective view of a detail of the rapid palatal expander of FIG. 3 relative to an actuator element.
Figure 19:
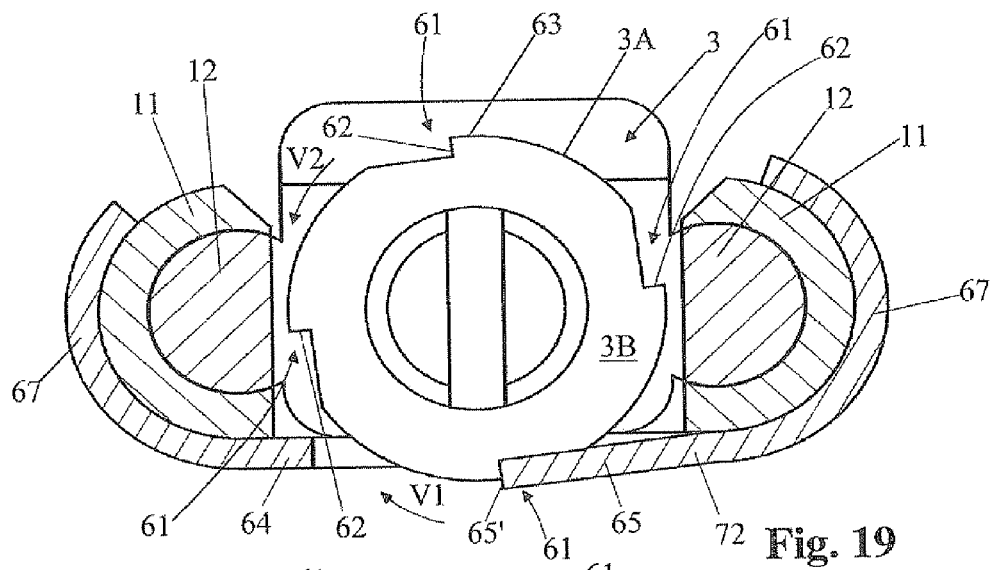
FIGS. 19, 20, 21 show a front view of the rapid palatal expander of FIG. 3 with several parts in section in order to better underline still other parts, in a sequence of three different positions reached by the head of the actuator element during the adjustment of its expansion in order to pass from one position of expansion to the next one.
Figure 20:
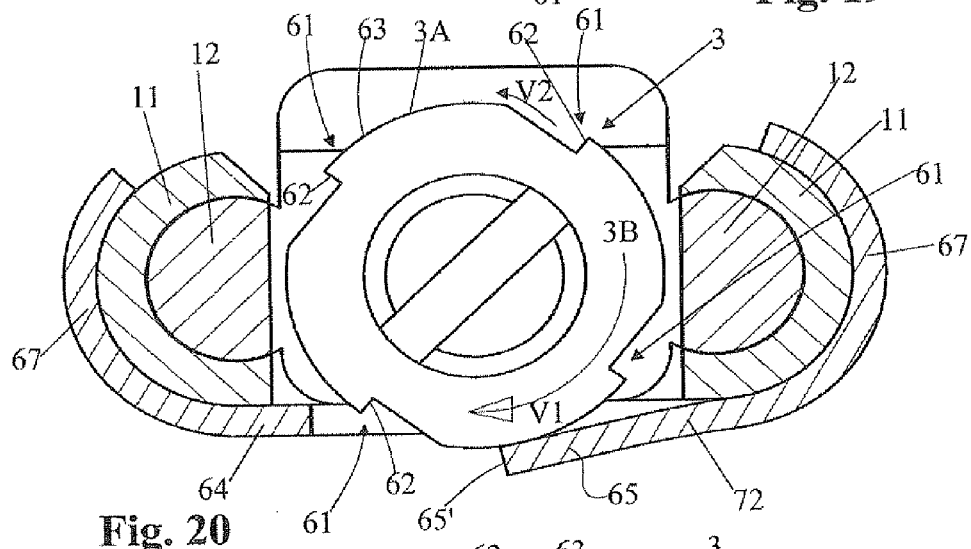
Figure 21:
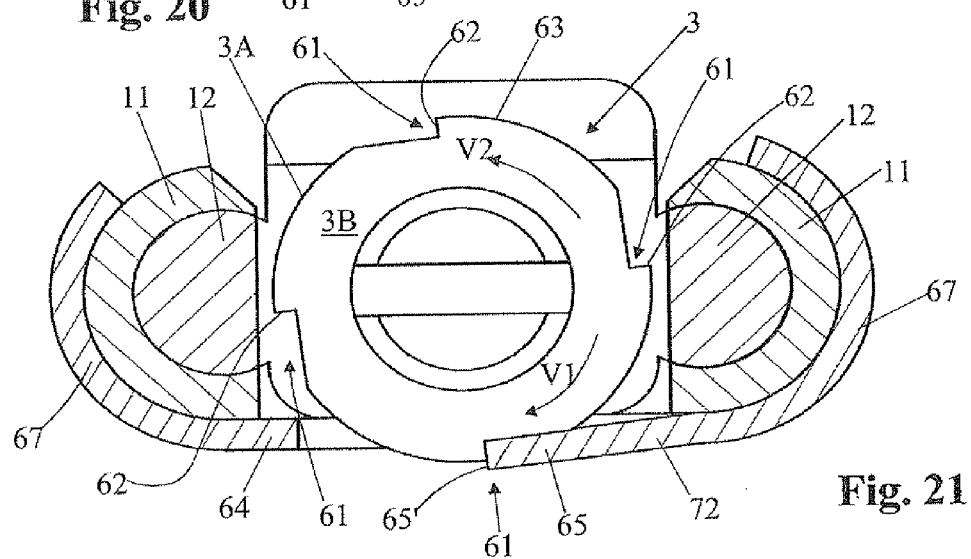
Figure 22:
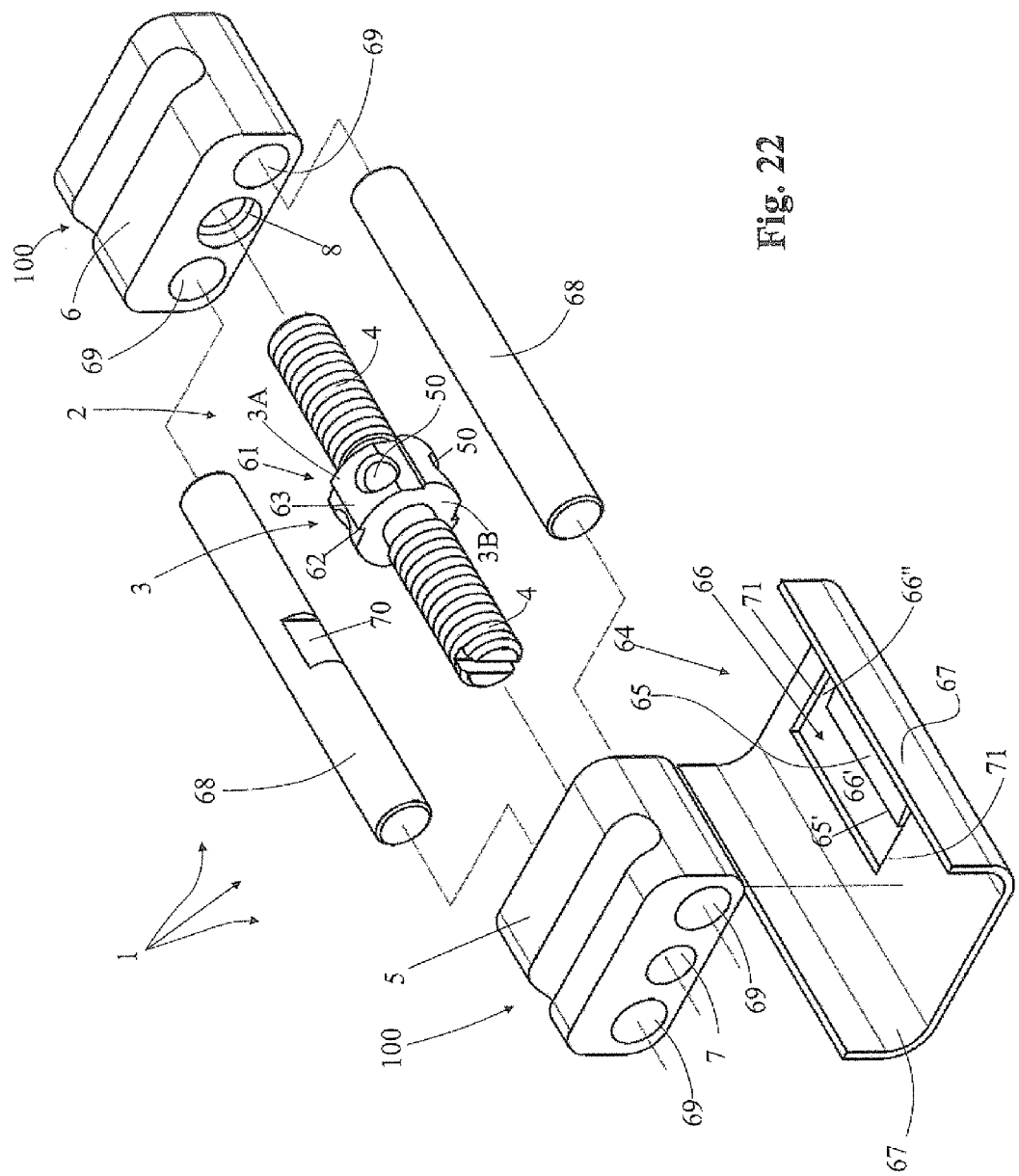
FIG. 22 shows an exploded perspective view of a second embodiment of a rapid palatal expander with several parts removed (the arms for transmitting the pressure to the teeth anchoring bands) in order to better illustrate other parts.
Figure 24:
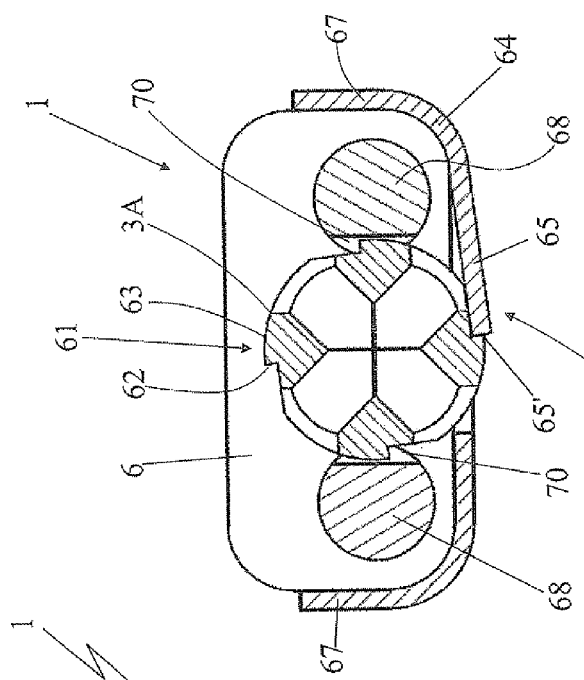
FIG. 24 shows a front view in section of the assembled expander of FIG. 22, carried out along the line XXIV-XXIV of FIG. 23.
Figure 23:
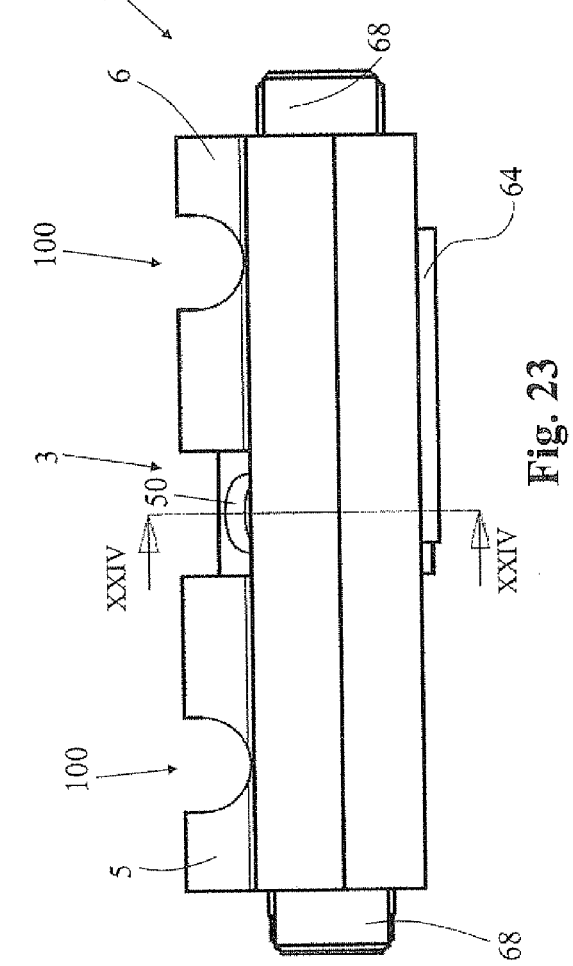
FIG. 23 shows a side view of the rapid palatal expander of FIG. 22, assembled and in closed position.

With reference to the set of drawings, reference number 1 indicates overall the rapid palatal expander, object of the present invention.

The rapid palatal expander 1, according to the present invention, is intended to be employed in a per se conventional manner in the orthodontics field for the pathological correction of a hypoplasia of the upper jaw, as already indicated above in the explanation of the field of application of the present finding.

It comprises an actuator element 2 with rod-shaped form, having a main extension in a longitudinal direction Y. Such element is provided with a drive head 3, central or placed in a substantially median position with respect to the longitudinal extension thereof, and with two stems 4 which are extended aligned with each other along such longitudinal direction Y, in opposite directions starting from the aforesaid drive head 3. The two stems 4 are provided with two threads oriented in opposite senses such that there is simultaneous screwing and unscrewing for both the stems 4 with respect to corresponding female threads on which they are engaged as described hereinbelow.

The head 3 has a substantially cylindrical peripheral surface 3A that is extended in a coaxial manner with respect to the longitudinal direction Y. Such peripheral surface 3A is delimited in the longitudinal direction Y by two lateral surfaces 3B transverse to the direction Y from which the stems 4 are extended in opposite directions.

The rapid palatal expander 1 further comprises, in a per se known manner, a first main body 5 and a second main body 6 provided with corresponding first front face 5A and second front face 6A, which are arranged parallel and facing each other.

Respective female threads 7 and 8 are obtained on such faces; such threads are aligned with each other, and each is engaged by one of the two threaded stems 4 of the actuator element 2.

Guide means 9 are then provided for guiding the simultaneous movement of the two main bodies 5, 6 in an advancement direction thereof which coincides with the longitudinal extension direction Y of the actuator element 2. The two main bodies 5, 6, being engaged to the stems 4 with opposite threads of a same actuator element 2, are moved closer to or further apart from each other following the rotation of the drive head 3, always in a synchronized manner in the same direction Y but in opposite senses.

More in detail the guide means 9, following the rotation of the drive head 3 in a first rotation sense V1 thereof, facilitate the movement of the two main bodies 5, 6 for at least one adjustment travel, from at least one collected position A, in which the main bodies 5, 6 are close to each other, to at least one expanded position B, in which the main bodies 5, 6 are spaced from each other.

Two or more rigid arms 10A are mechanically fixed to the two main bodies 5 and 6; such arms are extended in substantially opposite directions, and they are intended to interact, by means of teeth anchorage bands (e.g. molar bands) or other mechanical elements, with corresponding opposite portions of the dental arch.

The arms 10 are generally rigidly fixed in provided seats 100 of the main bodies 5, 6 by means of welding.

Operatively, once the rapid palatal expander 1 is installed in the mouth of the patient—with the bands gripping on the teeth in order to transmit thereto, through the arms 10, the thrust pressure of the main bodies 5, 6 kept spaced by the action of the actuator 2—one proceeds day after day to support the widening movement set by the actuator element 2 by means of the arms 10 to the rows of teeth of the dental arch of the patient, by rotating the drive head 3 of the actuator 2 by a predefined angle, usually an angle of 90 degrees each day or a multiple of 90 degrees each day.

In order to prevent the rotation of the drive head 3 of the actuator element 2 in the second rotation sense V2 opposite the first rotation sense V1, i.e. in the sense aimed to reapproach the two main bodies 5, 6, anti-rotation means are provided, generically indicated with the number 60, which comprise a plurality of longitudinal seats 61, obtained on the peripheral surface 3A of the drive head 3 in an equidistant manner along its circumferential extension around the longitudinal direction Y. Each longitudinal seat 61 has an abutment face 62 at least partially directed in the rotation sense V2 in order to abut against, as explained hereinbelow, an abutment element with which it is susceptible to interfere when such head 3 is forced to rotate in such second rotation sense V2. More in detail, the seats 61 are obtained by means of radial projections, connected to the body of the head 3 with a tapered connector portion 63 that becomes lower in the first rotation sense V1 and defining a step with elevation equal to the aforesaid abutment face 62.

According to the idea underlying the present invention, the anti-rotation means 60 further comprise a plate 64 rigidly mechanically connected to one of the two main bodies 5, 6 (directly or through elements integral therewith as explained hereinbelow) and provided with a flexible tab 65, which is extended along the longitudinal direction Y.

For example, in accordance with the embodiment illustrated in the enclosed figures, the main body bearing the plate 64 integrally connected is indicated with reference number 5; of course, it is also possible to instead provide for connecting such plate to the other main body, indicated with reference number 6.

The plate 64 is integrally connected to the first main body 5 in a manner so as to spatially arrange the flexible tab 65 elastically in abutment against the peripheral surface 3A of the drive head 3.

Such abutment is maintained for the entire adjustment travel that the first main body 5 carries out with the rotation of the drive head 3. Simultaneously, the flexible tab 65 is selectively engaged with its profile 65' in the longitudinal seats 61 at angular adjustment positions assumed by the drive head 3 along the adjustment travel.

Therefore, as the drive head 3 is made to rotate in the first rotation sense V1, during the normal progression of adjustments made each day to open the two bodies 5, 6 of the expander 1 and to continue the palate widening treatment of the patient, the flexible tab 65 of the plate 64 is moved following the translation of the first main body 5 to which it is fixed, by sliding on the peripheral surface 3A of the drive head 3. At the same time as the sliding of the plate 64 on the head 3, the rotation of the same head 3 takes place. Therefore, the plate 64 slides on a head 3 that rotates. The flexible tab 65 of the plate 64 consequently has extension such to be maintained in engagement on the head 3 for the entire slide travel of the main body 5 to which it is fixed; during such adjustment, the flexible tab 65 is first lifted on the connector portions 63 of the head 3 and then selectively snappingly falls, in engagement relationship, in the longitudinal seat 61. The rotation terminates when the head 3 has completed the angle corresponding to the desired adjustment, i.e. corresponding to the angular distance between the initial longitudinal seat 61 and the expected final seat.

The engagement relationship of the tab 65 in the seat 61 is such that the profile 65' of the tab 65 comes to abut against the abutment face 62 of the seat 61 for any one actuation of the head 3 in the second rotation sense V2 such to prevent the rotation of the head 3 in such second sense V2 (in particular in case of undesired and usually involuntary actuations due for example to normal patient chewing). The engagement relationship of the tab 65 in the seat 61 is also such that the profile 65' of the tab 65 is instead free to slide on the peripheral surface 3A of the rotation head 3 for actuations of the head 3 in the first rotation sense V1 (e.g. for the subsequent adjustments of the expansion of the bodies 5, 6).

With respect to the expanders of the prior art, the element of engagement with the rotating head that, in the case of the present invention, is constituted by the flexible tab 65, is extended over a greater section of the head 3, i.e. it engages it over its entire width, allowing a safer mechanical coupling, also without negatively affecting the expander in terms of greater size.

The plate 64 is advantageously obtained with a shaped sheet by means of cutting and bending. More in detail the plate 64 is provided with a window 66 that is delimited, at one side thereof, by the engagement profile 65' of the tab 65. The drive head 3 at least partially projects from the aforesaid window 66 and slides at its interior for the travel of the first main body 5.

Preferably, the flexible tab 65 interacts with the head 3 in its part that projects from the window. The tab 65 is connected to the remaining part of the plate 64 by means of a bend 72 that extends it in abutment against the portion of the head 3 that is extended outside the window 66.

Preferably, the aforesaid window 66 has overall C-shaped form, obtained with a longitudinal opening 66', with substantially rectangular form and which receives the drive head 3 along the aforesaid travel, and with two lateral notches 66" that delimit the longitudinal extension of the flexible tab 65.

The abovementioned guide means 9 can be obtained according to different embodiments.

In accordance with the embodiment illustrated in the FIGS. 1-21, the guide means 9 comprise a first pair of rods 11, which are rigidly fixed to the first main body 5, and in particular are obtained integral therewith, and are extended parallel to each other towards the second main body 6 starting from the first front face 5A, and a second pair of rods 12, which are in turn rigidly fixed to the second main body 6, and in particular in turn are obtained integral therewith, and are extended parallel to each other towards the first main body 5 starting from the second face 6A.

The two pairs of rods 11 and 12 are at least partially mutually engaged in a form relationship in order to guide the movement of the two main bodies 5, 6 with a single degree of freedom in the aforesaid longitudinal direction Y.

More in detail, the two pairs of rods are telescopically inserted inside each other, for example the first pair of rods 11 of female type, each with longitudinal cavity 11', at whose interior the rods of male type of the second pair of rods 12 are inserted in form relationship, such latter rods having section slightly less than the female rods 11 in order to slidably enter with minimum clearance in the longitudinal cavities 11' of the female rods 11.

Preferably, the latter rods of female type 11 are transversely more externally placed with respect to the rods of male type 11, in the transverse direction X orthogonal to the advancement direction Y of the main bodies 5, 6.

In addition, the rods of female type 11 preferably have C-shaped cross section with facing longitudinal concavities. Advantageously, the concavities of the female rods 11 are circumferentially extended for an angle greater than 180° in order to retain the male rods 12 constrained at their interior, also with respect to shifting transverse to the advancement direction Y of the main bodies 5, 6 and lying in the plane of the rods 11, 12.

The rods of the two pairs of rods 11, 12 project from the relative first and second front face 5A, 6A but are also preferably extended on the two lateral flanks of the two main bodies 5, 6 indicated with reference numbers 5C and 6C. More particularly, the two female rods 11 define two corresponding tubular cavities at the two flanks of the first main body 5 while the two male rods 12 define two corresponding rails or lobes with convexities aimed transversely towards the outside, and counter-shaped with respect to the facing concavities aimed towards the interior of the female rods 11.

The two main bodies 5 and 6 are controlled to be moved by the rotation of the drive head 3 in the first rotation sense V1 between the collected position A or minimum expansion position, in which the rods of the pair of male rods 12 are substantially entirely inserted in the pair of female rods 11, and an expanded position or maximum expansion position B, in which the rods of the pair of male rods 12 penetrate the cavities of the female rods 11 only for a reduced terminal portion thereof.

Preferably, in the collected position A, the free ends of the female rods 11 and male rods 12 arrive in proximity to, or even flush with, the first and second rear face 5B, 6B respectively of the two main bodies 5 and 6.

The plate 64 is rigidly and integrally connected to one of the two main bodies 5, 6 through a fixing thereof as a bridge between one of the two pairs of rods 11, 12. Preferably, and in accordance with the embodiment illustrated in the enclosed FIGS. 1-21, the plate 64 will be fixed as a bridge between the two female rods 11 arranged outside the more internal rods of male type 12. The fixing is advantageously obtained for example with laser welding, between the female rods 11 and the longitudinal edges 67 of the plate 64, advantageously for such purpose bent with corresponding form on the external profile of the female rods 11.

In accordance with an embodiment variant, not illustrated in detail since it is sufficiently described as reported hereinbelow, the guide means 9 can provide for only one rod 11 fixed to the first main body 5 and only one rod 12 fixed to the second main body 6, such rods 11 and 12 mutually engaged to slide parallel one on the other or one within the other, as specified above, along the aforesaid advancement direction Y.

In such case, the plate 64 will preferably be directly fixed to one of the two main bodies 5, 6, even if it could of course be fixed to only one of the two rods 11 and 12 though with lower rigidity and precision.

In accordance with the embodiment illustrated in the FIGS. 22-29, the guide means 9 comprise a single pair of slidable rods 68, which are slidably inserted in opposite and aligned through holes 69 obtained in the main bodies 5, 6. In accordance with this embodiment, the plate 64 is directly fixed to a main body 5, 6 and in particular to the body indicated with 5 in the enclosed figures. According to such embodiment, the rods are advantageously provided in a median section thereof with two opposite cavities 70, in which a peripheral portion of the drive head 3 is inserted in order to maintain the pair of rods centered in intermediate position between the main bodies 5, 6 during the driving of the actuator element. In accordance with this embodiment, indeed, the slidable rods 68 remain stopped and constrained to the head 3, while the main bodies 5, 6 slide with respect to the rods, being unthreaded from the slidable rods 68 through the through holes 69.

In accordance with a particularly advantageous characteristic of the present invention, the presence of the plate 64 with the relative window 66 allows obtaining the end stops of the main bodies 5, 6 in an extremely easy manner, such end stops determining the collected A and expanded B positions of the main bodies 5, 6.

More in detail, the window 66 has at least one side wall 71 which acts as an end stop for the travel of the first main body 5 (in accordance with the embodiment of FIGS. 30, 31) and preferably has two opposite side walls 71 which each act as end stop for the travel of the first main body 5, defining the final collected A and expanded B positions of the two main bodies 5, 6 along their longitudinal advancement direction Y following the rotation of the drive head 3 in the first rotation sense V1 for the opening of the expander (in accordance with the first two embodiments of FIGS. 1-21 and 22-29).

The drive head 3 is advantageously substantially cylindrical, even if the seats 61 modify the profile thereof with respect to a perfectly circular section, and it is provided, in a per se already known manner, with a plurality of first holes 50 with radial extension, arranged circumferentially in an equidistant manner, within which a key can be engaged (not illustrated since of per se known type) in order to impart a rotation to the head 3 aimed to adjust the expansion of the expander 1 through its arms 10 on the palate arch. Preferably, there are four of such first holes 50 arranged angularly at 90 degrees from each other.

The drive head 3 is housed in a seat 14 delimited in a direction transverse to the extension direction Y, between the mutually engaged rods of the two pairs of rods 11, 12 (i.e. in particular between one male/female pairing of rods and the other male/female pairing of rods), and in the extension direction Y, between the first and the second front face 5A, 6A of the two main bodies 5, 6.

The seat 14 is further delimited by the aforesaid plate 64 in an upper plane defined by the longitudinal direction and by the transverse direction.

Figure 32:
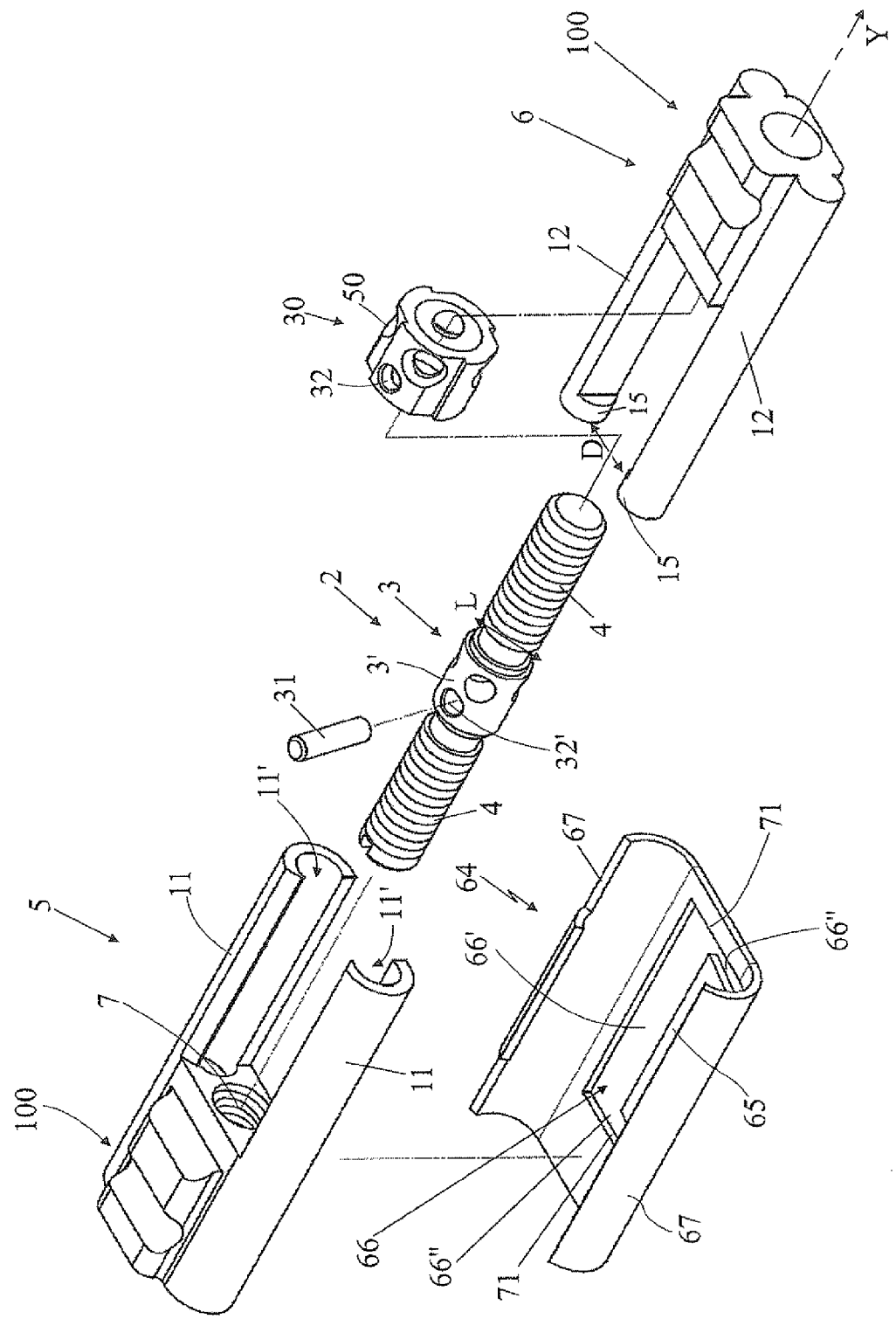
FIG. 32 shows an exploded view of a fourth embodiment of a rapid palatal expander with several parts removed (the arms for transmitting the pressure to the teeth anchoring bands) in order to better illustrate other parts.

In accordance with an advantageous characteristic of the present invention illustrated in FIGS. 32-34, the end stop in the opening of the palatal expander 1 is obtained, as an alternative to that defined by the plate 64 or in addition thereto for greater safety, by means of at least one nose section 15, arranged at a free end of at least one rod of at least one of the two pairs of rods 11, 12 and projecting towards the other rod of the same pair of rods 11, 12, so as to come to abut against an enlarged portion of the drive head 3.

More in detail, the nose section 15 is obtained at the end of at least one rod of the more internal pair of rods which preferably, in accordance with the embodiment illustrated in the enclosed figures, is constituted by the pair of male rods 12.

Preferably, two nose sections 15 are provided which are directed facing against each other at the free ends of both rods of the pair of male rods 12, in order to balance the end stop forces with respect to a median plane of the expander 1 passing through the extension Y axis of the actuator element 2 and orthogonal to the plane of the rods 11, 12.

The abovementioned nose sections 15 are obtained integral with the relative pair of male rods 12 and with the relative second main body 6. Otherwise, the nose sections 15 can be obtained at the free ends of the pair of female rods 11.

In order to allow a facilitated assembly of the palatal expander 1, object of the present invention, without having to bend the male rods 12 (provided with considerable rigidity) in order to allow the passage of the drive head 3, the latter is preferably composed of a central core 3' with width L less than the minimum distance D that lies between the more internal rods of the two pairs of rods 11, 12; in other words, in accordance with the particular embodiment illustrated in the enclosed figures, width L is less than the limited distance D that lies between the nose sections 15 provided at the free ends of the two male rods 12. In this manner, the actuator element 2 thus obtained with the single core 3' is in all parts thereof narrower than the distance between the internal rods of male type 12, which laterally delimit the seat 14, and can be easily inserted in assembly step between the two main bodies 5 and 6 and screwed thereto.

Subsequently, an enlarged portion 30 of the drive head 3 is mechanically associated with the core 3', which interferes with the nose sections 15 (having width greater than D) in order to obtain the end stop in the opening of the expander 1. Of course, the enlarged portion 30 is associated with the central core 3', only after the latter has been moved for the screwing of the stems 4 from an initial position adjacent to the nose sections 15 to a position no longer facing the nose sections 15.

In order to widen the core 3', of substantially cylindrical shape, various embodiments are provided for.

In accordance with the embodiment in FIGS. 32-34, the enlarged portion has the form of an annular crown indicated with 30, which can be mechanically and peripherally associated with the core 3' for example by means of a pin 31 that is forcibly inserted in a radial hole 32 obtained with a through opening made on the crown 30 and with a hole 32' aligned with the opening and provided on the core 3'.

Advantageously, the abovementioned first holes 50 for the engagement of the key which determines the rotation of the drive head 3 are also obtained with a through opening made in the crown 30 and with a hole aligned with the opening provided in the core 3'.

Of course, in the practical obtainment thereof, the rapid palatal expander 1 can assume shapes and configurations that are different from that illustrated above, without departing from the present protective scope.

In addition, all details can be substituted by technically equivalent elements and the size, shapes and materials used can be of any type according to requirements.

The invention claimed is:

1. A rapid palatal expander which comprises:
a rod-shaped actuator element (2) having main extension in a longitudinal direction (Y), wherein the rod-shaped actuator element (2) is provided with a drive head (3), the drive head (3) being in a median position of the rod-shaped actuator element (2) and having a substantially cylindrical peripheral surface (3A) coaxial with said longitudinal direction (Y), and wherein the rod-shaped actuator element (2) is provided with two threaded stems (4) which are extended aligned in opposite directions from said drive head (3) and have threads configured in opposite threading orientations,
a first main body (5) provided with a first front face (5A) and a second main body (6) provided with a second front face (6A), wherein the first front face (5A) is opposite to the second front face (6A), and wherein the first front face (5A) and the second front face (6A) have respective aligning female threads (7, 8), each female thread (7, 8) being engaged by the respective threaded stem (4) of said rod-shaped actuator element (2);
guide means (9) for guiding a simultaneous movement of said first and second main bodies (5, 6) along said longitudinal direction (Y) following a rotation of said drive head (3) in a first rotation direction (V1) for at least one adjustment travel of said first and second main bodies (5,6), from at least one collected position (A), in which said first and second main bodies (5, 6) are close to each other, to at least one expanded position (B), in which said first and second main bodies (5, 6) are spaced from each other;
anti-rotation means (60) configured for preventing the rotation of the drive head (3) of said actuator element in a second rotation direction (V2) opposite the first rotation direction (V1), wherein the anti-rotation means (60) comprises a plurality of equidistant longitudinal seats (61) positioned on the peripheral surface (3A) of said drive head (3), each longitudinal seat (61) of the plurality of equidistant longitudinal seats (61) having an abutment face (62) at least partially directed in said second rotation direction (V2);
wherein said anti-rotation means (60) further comprises:
at least one plate (64) mechanically and rigidly connected to the first main body (5) of said first and second main bodies (5, 6), wherein the plate (64) is provided with a flexible tab (65) having an engagement profile (65'), wherein the flexible tab (65) is extended in said longitudinal direction (Y) and is arranged elastically in abutment against the peripheral surface (3A) of said drive head (3) for an adjustment travel of said first main body (5), said flexible tab (65) being configured to be selectively engaged with the engagement profile (65') in said longitudinal seats (61) of the plurality of equidistant longitudinal seats (61) at angular adjustment positions assumed by said drive head (3) along said adjustment travel.

2. The rapid palatal expander according to claim 1, wherein said plate (64) is provided with a window (66), delimited by the engagement profile (65') of said tab (65), and wherein said drive head (3) slides within said window (66) for the adjustment travel of said first main body (5).

3. The rapid palatal expander according to claim 2, wherein said window (66) has C-shaped form, wherein the window (66) is provided with a longitudinal opening (66') that receives said drive head (3) along said travel path, and the window (66) is provided with two lateral notches (66") that delimit said flexible tab (65).

4. The rapid palatal expander according to claim 1, wherein said guide means (9) comprise at least one first pair of rods (11) which are fixed to said first main body (5) or are integral therewith with said first main body (5), and wherein from the first front face (5A) of such first main body (5), such first pair of rods (11) are extended parallel to each other towards said second main body (6); said plate (64) being fixed as a bridge between said first pair of rods (11).

5. The rapid palatal expander according to claim 4, wherein said plate (64) has longitudinal edges (67), and wherein each of the longitudinal edges (67) of said plate (64) is fixed to a corresponding said rod (11) of the first pair of rods (11).

6. The rapid palatal expander according to claim 4, wherein said guide means (9) further comprise:
a second pair of rods (12), which are fixed to said second main body (6) or are integral with said second main body (6), and wherein from the second front face (6A) of such second main body (6), such second pair of rods (12) are extended parallel to each other towards said first main body (5);
wherein said first pair of rods (11) and said second pair of rods (12) are at least partially mutually slidably engaged in a form relationship for guiding the simultaneous movement of said first main body (5) and second main body (6) with a single degree of freedom in the aforesaid longitudinal direction (Y).

7. The rapid palatal expander according to claim 6, wherein the rods (11) of said first pair of rods (11) are hollow, and wherein the rods (12) of said second pair of rods (12) are slidably inserted in a form engagement within cavities of the rods (11) of said first pair of rods (11); said plate (64) being fixed at the longitudinal edges (67) of the plate (64) to said first pair of rods (11).

8. The rapid palatal expander according to claim 6, wherein the rods (11) of said first pair of rods (11) are hollow, and wherein said plate (64) is fixed as a bridge, by means of the longitudinal edges (67) of the plate (64), to said first pair of rods (11), wherein the first pair of rods (11) are arranged outside said second pair of rods (12).

9. The rapid palatal expander according to claim 2, wherein said drive head (3) projects outside said window (66), and wherein said flexible tab (65) has a bend (72) that is extended outside said window (66) towards said drive head (3).

10. The rapid palatal expander according to claim 2, wherein said window (66) has at least one side wall (71) which acts as an end stop for the adjustment travel of said first main body (5).

11. The rapid palatal expander according to claim 10, wherein said window (66) has two opposite side walls (71), wherein each side wall (71) acts as an end stop for the adjustment travel of said first main body (5), and wherein the side walls (71) define the final positions of the collected (A) and expanded (B) positions of said first and second main bodies (5, 6) along said longitudinal direction (Y) following the rotation of said drive head (3) in said first rotation direction (V1).

12. The rapid palatal expander according to claim 6, further comprising a seat (14),
wherein the drive head (3) of said rod-shaped actuator element (2) is housed in the seat (14), and
wherein the seat (14) is delimited:
in a transverse direction transverse to said longitudinal direction (Y), between the mutually engaged rods of said first and second pairs of rods (11, 12),
in the direction of said longitudinal direction (Y), between the first and second front face (5A, 6A) of said first and second main bodies (5, 6) and
by said plate (64), in an upper plane defined by said longitudinal direction (Y) and by said transverse direction.

13. The rapid palatal expander according to claim 1, wherein said guide means (9) comprise at least one pair of slidable rods (68), which are slidably inserted in opposite, aligned through holes (69) obtained in said first and second main bodies (5, 6); said pair of slidable rods (68) being mechanically constrained to said drive head (3) along said longitudinal direction (Y) in order to maintain said pair of slidable rods (68) centered in intermediate position between said first and second main bodies (5, 6) during a driving of said rod-shaped actuator element (2).

14. The rapid palatal expander according to claim 6, wherein at least one free end of at least one rod of at least one pair, of said first and second pairs of rods (11, 12) is provided with a nose section (15) that is internally projecting towards the other rod of said pair of said first and second pairs of rods (11, 12), wherein the nose section (15) transversely defines a reduced distance (D) and is configured to abut against an enlarged portion (30) of said drive head (3) in order to define an end stop in an opening of said expander (1).

15. The rapid palatal expander according to claim 14, wherein said at least one nose section (15) is obtained on at least one rod of a more internal pair of said first and second pairs of rods (11, 12), so as to define said reduced distance (D) between the rods of said internal pair.

16. The rapid palatal expander according to claim 14, wherein said drive head (3) comprises a central core (3') having a width (L) less than said reduced distance (D), wherein the a central core (3') is susceptible to translate along said longitudinal direction (Y) without interfering with said nose section (15), and wherein said enlarged portion (30) is mechanically associated with said core (3') and is configured to interfere with said nose section (15) along said longitudinal direction (Y) in order to obtain said end stop.

17. The rapid palatal expander according to claim 16, wherein said core (3') has cylindrical form and wherein said enlarged portion (30) has annular ring form, such enlarged portion (30) being mechanically fixed on the external peripheral surface of core (3').

18. The rapid palatal expander according to claim 1, wherein each seat (61) comprises:
a radial projection defining a step which defines the abutment face (62) and has elevation equal to the abutment face (62), and
a tapered connector portion (63) which connects the radial projection to the peripheral surface (3a) of the drive head (3) and becomes lower in the first rotation direction (V1).

19. The rapid palatal expander according to claim 1, wherein the flexible tab (65) engages the longitudinal seat (61) so that the engagement profile (65') of the flexible tab (65) abuts against the abutment face (62) of the longitudinal seat (61) for actuations of the drive head (3) in the second rotation direction (v2) such to prevent the rotation of the drive head (3) in such second direction (v2), and wherein the flexible tab (65) engages the longitudinal seat (61) so that the engagement profile (65') of the flexible tab (65) is free to slide on the peripheral surface (3A) of the drive head (3) for actuations of the drive head (3) in the first rotation direction (V1).

\* \* \* \* \*